(12) United States Patent
Kawahara et al.

(10) Patent No.: US 7,585,298 B2
(45) Date of Patent: Sep. 8, 2009

(54) ENDOSCOPIC HIGH-FREQUENCY KNIFE

(75) Inventors: Yoshiro Kawahara, Okayama (JP);
Hiroaki Shibata, Saitama (JP)

(73) Assignee: HOYA Corporation, Tokyo (JP)

( * ) Notice: Subject to any disclaimer, the term of this patent is extended or adjusted under 35 U.S.C. 154(b) by 456 days.

(21) Appl. No.: 11/344,078

(22) Filed: Feb. 1, 2006

(65) Prior Publication Data

US 2006/0173450 A1    Aug. 3, 2006

(30) Foreign Application Priority Data

Feb. 2, 2005    (JP)    ............................. 2005-025798

(51) Int. Cl.
*A61B 18/14*    (2006.01)
(52) U.S. Cl. .......................... 606/45; 606/46
(58) Field of Classification Search .............. 606/45–47
See application file for complete search history.

(56) References Cited

U.S. PATENT DOCUMENTS

| 4,325,374 | A | * | 4/1982 | Komiya | ........................ 606/47 |
| 5,075,062 | A | * | 12/1991 | Karpiel | ..................... 264/171.2 |
| 5,643,294 | A | * | 7/1997 | Tovey et al. | ................. 606/148 |
| 5,984,920 | A |  | 11/1999 | Steinbach | |
| 6,190,384 | B1 |  | 2/2001 | Ouchi | |
| 6,331,166 | B1 | * | 12/2001 | Burbank et al. | ............... 606/45 |
| 6,514,248 | B1 | * | 2/2003 | Eggers et al. | ................. 606/41 |
| 6,712,817 | B1 | * | 3/2004 | Goto et al. | ..................... 606/47 |

| 2002/0072688 | A1 | 6/2002 | Burbank et al. |
| 2005/0049454 | A1 | 3/2005 | Ouchi |
| 2005/0261675 | A1 | 11/2005 | Shibata |

FOREIGN PATENT DOCUMENTS

| JP | 61-007694 | 6/1986 |
| JP | 05-176940 | 7/1993 |

OTHER PUBLICATIONS

English language abstract of JP 05-176940.
U.S. Appl. No. 11/344,079 to Shibata, filed Feb. 1, 2006.

* cited by examiner

*Primary Examiner*—Lee S Cohen
(74) *Attorney, Agent, or Firm*—Greenblum & Bernstein, P.L.C.

(57) ABSTRACT

An endoscopic high-frequency knife includes an insulating flexible sheath, a conductive wire inserted into the insulating flexible sheath, and a high-frequency cutting electrode. The high-frequency cutting electrode is installed in the endoscopic high-frequency knife so that an outer surface of the high-frequency cutting electrode is exposed at a side surface of the insulating flexible sheath in the vicinity of an end thereof. The conductive wire is electrically connected with the high-frequency cutting electrode. The insulating flexible sheath includes a distal portion and a proximal portion which are separated from each other. The distal portion and the proximal portion are freely rotatable relative to each other. A portion of the conductive wire in the vicinity of an end thereof is fixed to the distal portion to thereby prevent the distal portion from separating from the conductive wire even if the high-frequency cutting electrode breaks.

10 Claims, 5 Drawing Sheets

ENDOSCOPIC HIGH-FREQUENCY KNIFE

BACKGROUND OF THE INVENTION

1. Field of the Invention

The present invention relates to an endoscopic high-frequency knife which is inserted into a treatment tool insertion channel of an endoscope to be used as a surgical instrument for an endoscopic mucosal resection (EMR), and the like.

2. Description of the Related Art

A technique of peeling a resection part (e.g., an affected part) with the use of an endoscopic high-frequency knife by firstly injecting physiological saline, or the like, into a submucosa under the resection part to swell (raise) the resection part and subsequently cutting the root of the swelled resection part with the use of the endoscopic high-frequency knife is known in the art as an endoscopic mucosal resection (EMR). As an endoscopic high-frequency knife suitable for the use of such a surgical technique, an endoscopic high-frequency knife to which a high-frequency cutting electrode is installed so that an outer surface of the high-frequency cutting electrode is exposed at a side surface of the insulating flexible sheath in the vicinity of the end thereof is known in the art. This type of endoscopic high-frequency knife is disclosed in Japanese utility model gazette No. 61-7694.

FIG. 7 shows a state in which an endoscopic mucosal resection is performed with the use of a conventional endoscopic high-frequency knife such as that mentioned above. In this state, the root of a swelled resection part 100 of a mucosa is sectioned by a high-frequency cutting electrode 2 in an energized state thereof by swinging the end of a flexible sheath 1, which projects from the distal end of a treatment tool insertion channel of an endoscope (not shown), by manipulating a manual operation portion of the endoscope.

However, in the case where the swelled resection part 100 is greater than the high-frequency cutting electrode 2 as shown in FIG. 7, the swelled resection part 100 cannot be resected completely by a single swing of the end of the flexible sheath 1, and accordingly, it is necessary to swing the end of the flexible sheath 1 repeatedly while gradually changing the incisional position after returning the flexile sheath 1 to its initial position.

However, since the flexible sheath 1 may hit the swelled resection part 100 if one tries to return the flexible sheath 1 directly to its initial position after partly resection the swelled resection part 100 with the high-frequency cutting electrode 2, the endoscope needs to be manipulated so as to return the flexible sheath 1 to its original position in an indirect manner to prevent the flexible sheath 1 from hitting the swelled resection part 100. Hence, it is very troublesome to set the flexible sheath 1 precisely at the subsequent point of commencement of the resection operation.

SUMMARY OF THE INVENTION

The present invention provides an endoscopic high-frequency knife with which one can easily make numerous consecutive incisions in a swelled resection part in a short time, and which offers a superior level of structural safety even if a high-frequency cutting electrode of the endoscopic high-frequency knife breaks.

According to an aspect of the present invention, an endoscopic high-frequency knife is provided, including an insulating flexible sheath, a conductive wire inserted into the insulating flexible sheath, and a high-frequency cutting electrode. The high-frequency cutting electrode is installed in the endoscopic high-frequency knife so that an outer surface of the high-frequency cutting electrode is exposed at a side surface of the insulating flexible sheath in the vicinity of an end thereof. The conductive wire is electrically connected with the high-frequency cutting electrode. The insulating flexible sheath includes a distal portion and a proximal portion which are separated from each other at a separation position behind the high-frequency cutting electrode on a proximal side thereof in the vicinity of the end of the insulating flexible sheath. The distal portion and the proximal portion are connected to each other at the separation position to be freely rotatable relative to each other about a common axis which is also common with an axis of the insulating flexible sheath, so that the distal portion rotates about the common axis by rotating the conductive wire from a proximal end of the proximal portion. A portion of the conductive wire in the vicinity of an end thereof is fixed to the distal portion to thereby prevent the distal portion from separating from the conductive wire even if the high-frequency cutting electrode breaks.

It is desirable for the endoscopic high-frequency knife to include a fixing member which is fixed to the conductive wire in the vicinity of the end thereof, wherein the conductive wire is fixed to the distal portion by press-fitting the fixing member into the distal portion.

It is desirable for an axial groove to be formed in the fixing member from an outer peripheral surface of the fixing member to an axis thereof, the axial groove being elongated throughout the length of the fixing member and is parallel to the axis of the fixing member, wherein the conductive wire is inserted into the axial groove so as to be fixed to the fixing member.

It is desirable for the conductive wire to include a stranded wire including a plurality of wire strands, wherein at least one wire strand of the plurality of wire strands is extended and bent rearward in the vicinity of the end of the distal portion to be partly formed as the high-frequency cutting electrode. A rearward-extending part of the rearwardly bent the wire strand passes through the axial groove to extend rearward from the fixing portion.

It is desirable for a core strand of the conductive wire to be extended to be partly drawn out of the distal portion to serve as the high-frequency cutting electrode.

It is desirable for an end of the core strand of the conductive wire, which is positioned in the proximal portion behind the high-frequency cutting electrode, to be wound loosely around the conductive wire.

It is desirable for the fixing member to have a substantially cylindrical shape and to include a small-diameter portion and a large-diameter portion provided at one end of the small-diameter portion. An outer diameter of the small-diameter portion is substantially the same as an inner diameter of the distal portion of the insulating flexible sheath. An outer diameter of the large-diameter portion is slightly greater than the inner diameter of the distal portion, so that an outer peripheral surface of the fixing member is stepped between the small-diameter portion and the large-diameter portion.

It is desirable for the fixing member to be swaged with the conductive wire, the conductive wire being positioned in the axial groove of the fixing member so as to fix the conductive wire to the fixing member.

It is desirable for the high-frequency cutting electrode to extend in a direction substantially parallel to an axis of the distal portion.

It is desirable for the distal portion to include two holes which are provided apart from each other in the direction substantially parallel to the axis of the distal portion, the outer surface of the high-frequency cutting electrode being exposed at the side surface of the insulating flexible sheath via the two holes.

It is desirable for the wire strands to be partly sheathed in the vicinity of an end thereof by a sheath which prevents the conductive wire from becoming frayed, wherein the fixing member is fitted directly on the sheath.

In an embodiment, an endoscopic high-frequency knife is provided, including an insulating flexible sheath including a proximal portion and a distal portion which is connected to the proximal portion to be freely rotatable on an axis of the distal portion relative to the proximal portion; and a conductive wire inserted into the insulating flexible sheath so that a part of the conductive wire is exposed to the outside of the distal portion to serve as a high-frequency cutting electrode. Rotating the conductive wire on an axis thereof relative to the insulating flexible sheath therein causes the distal portion to rotate on the axis thereof relative to the proximal portion. A portion of the conductive wire in the vicinity of an end thereof is fixed to the distal portion via a substantially cylindrical fixing member which is press-fitted in between the conductive wire and the distal portion.

According to the present invention, since the endoscopic high-frequency knife is constructed so that the distal portion rotates on the axis thereof by rotating the conductive wire from the proximal end side of the proximal portion, one can reorient the high-frequency cutting electrode to change the incisional position for the subsequent incising operation instantly by changing the orientation of the high-frequency cutting electrode by approximately 180 degrees each time an incision has been made in a swelled resection part. Accordingly, one can quite easily make numerous consecutive incisions in a swelled resection part of a mucosa in a short time with the endoscopic high-frequency knife according to the present invention; moreover, since the distal portion is fixed relative to the conductive wire, there is no possibility of the distal portion from falling off in the body of a patient even if the high-frequency cutting electrode breaks during the resection operation in the patient body, which ensures a high level of structural safety.

The present disclosure relates to subject matter contained in Japanese Patent Application No. 2005-25798 (filed on Feb. 2, 2005) which is expressly incorporated herein by reference in its entirety.

BRIEF DESCRIPTION OF THE DRAWINGS

The present invention will be discussed below in detail with reference to the accompanying drawings, in which.

DESCRIPTION OF THE PREFERRED EMBODIMENT

Figure 1:
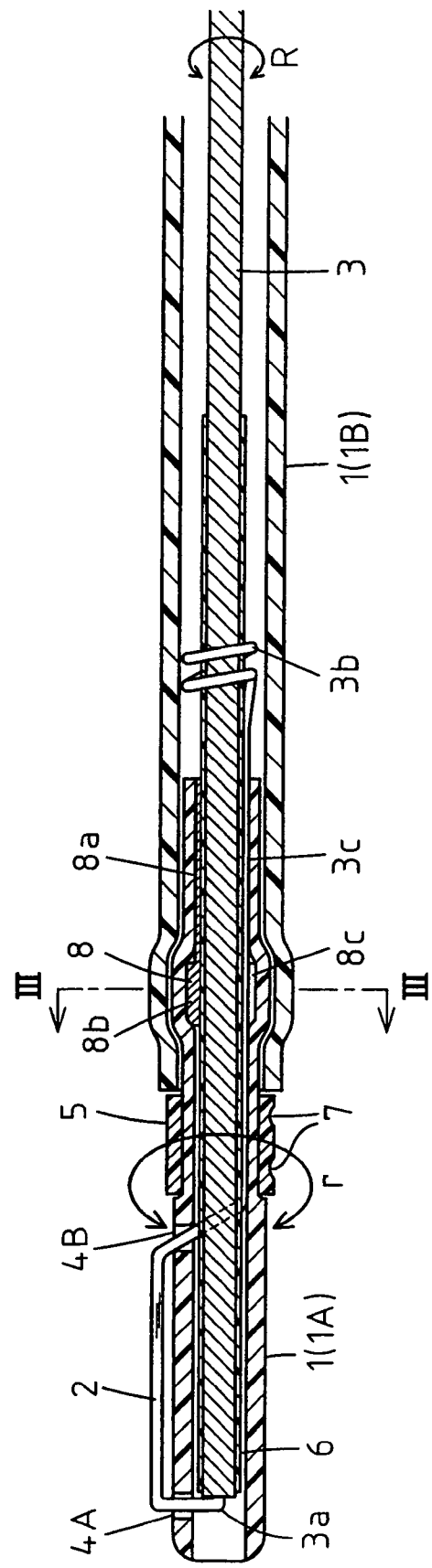
FIG. 1 is an axial sectional view of an end portion of an embodiment of an endoscopic high-frequency knife according to the present invention.
Figure 2:
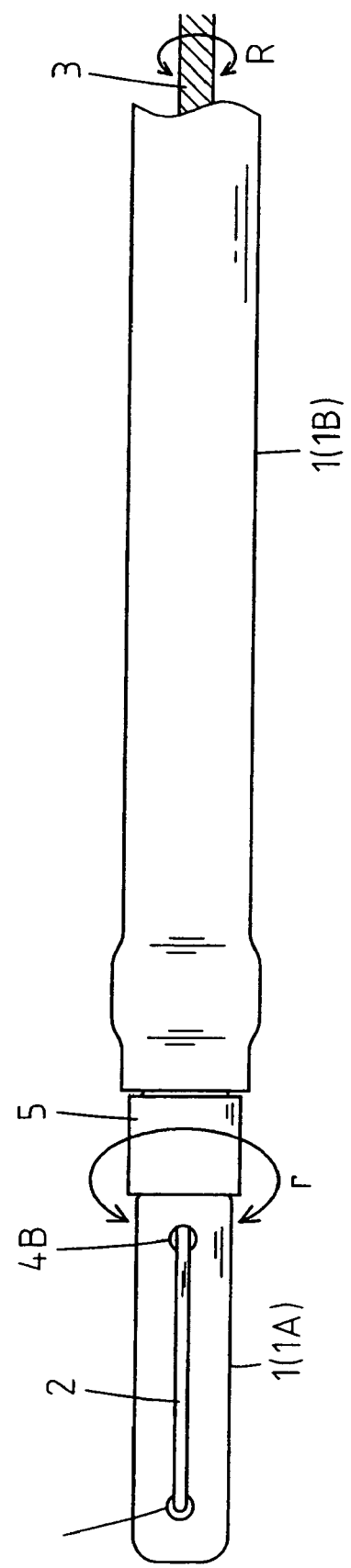
FIG. 2 is a plan view of the end portion of the endoscopic high-frequency knife shown in FIG. 1.

FIGS. 1 and 2 show an end portion (distal end portion) of an embodiment of an endoscopic high-frequency knife according to the present invention. The endoscopic high-frequency knife is provided with an insulating flexible sheath 1, a high-frequency cutting electrode 2 and a conductive wire (conductive stranded wire) 3. The insulating flexible sheath 1 is a flexible tube made of resin such as polytetrafluoroethylene (PTFE). The high-frequency cutting electrode 2 is installed in the endoscopic high-frequency knife so that an outer surface of the high-frequency cutting electrode 2 is exposed at a side surface of the flexible sheath 1 in the vicinity of the end thereof. The conductive wire 3 which is inserted into the flexible sheath 1 is joined to the high-frequency cutting electrode 2 to establish electrical connection therewith.

The flexible sheath 1 is separated into two portions: a distal portion 1A and a proximal portion 1B in the vicinity of the distal end of the flexible sheath 1 a little away from the high-frequency cutting electrode 2 toward the proximal end side of the flexible sheath 1 (e.g., at a position 3 to 10 centimeters away from the end of the flexible sheath 1).

Specifically, the proximal portion 1B is formed to be, e.g., approximately 1.5 to 3 millimeters in diameter and approximately 1 to 2 meters in length, and the distal portion 1A is formed to have an outer diameter that allows the distal portion 1A to be loosely fitted into the distal end of the proximal portion 1B by a length of approximately 1 to 2 centimeters and to be capable of rotating freely on the axis of the distal portion 1A relative to the proximal portion 1B.

In the present embodiment, the conductive wire 3 is a stranded wire consisting of a plurality of wire strands (conductive wire strands). The plurality of wire strands consist of a straight core strand and the remaining wire strands (e.g., five or six wire strands) which surround the straight core strand. The end of the core strand is extended from the end of the stranded wire to be partly formed as the high-frequency cutting electrode 2. The high-frequency cutting electrode 2 extends in a direction substantially parallel to an axis of the distal portion 1A. A portion of the conductive wire 3 in the vicinity of the end thereof is sheathed with a sheath 6 which prevents the conductive wire 3 from becoming frayed and from expanding radially. One or more wire strands of the conductive wire 3 other than the core strand of the conductive wire 3 can be extended from the end of the stranded wire to be formed as the high-frequency cutting electrode 2.

The distal portion 1A is provided, on the periphery thereof in the vicinity of the opposite ends of the distal portion 1A, respectively, with a pair of through-holes (radial holes) 4A and 4B, which are spaced from each other in the lengthwise direction (axial direction) of the distal portion 1A. An extended part 3a of the core strand of the conductive wire 3 is drawn out of the distal portion 1A through the through-hole 4A and bent backward (rightward as viewed in FIG. 1). Subsequently, the end of the backwardly bent portion of the extended part 3a is drawn back into the distal portion 1A through the through-hole 4B so that a portion of the extended part 3a which is exposed to the outside of the distal portion 1A between the pair of through-holes 4A and 4B serves as the high-frequency cutting electrode 2.

The end 3b of an extended part 3c of the core strand that is drawn into the distal portion 1A through the through-hole 4B extends backward up into the proximal portion 1B and is wound loosely around the conductive wire 3 inside the proximal portion 1B in the vicinity of the distal end thereof without being fixed to the conductive wire 3.

The endoscopic high-frequency knife is provided, on an outer peripheral surface of the distal portion 1A in close vicinity of the end of the proximal portion 1B, with a stopper tube 5 which is firmly fitted on the distal portion 1A, e.g., by being heat-shrunk thereon. The stopper tube 5 prevents the distal portion 1A from being further drawn into the proximal portion 1B when an external force which makes the distal portion 1A move in the axial direction thereof relative to the proximal portion 1B is exerted on the distal portion 1A.

The endoscopic high-frequency knife is provided with indicia (marks) 7 on the stopper tube 5 in a rearward axial direction extending from the distal portion 1A on the circumferentially opposite side of the distal portion 1A from the high-frequency cutting electrode 2.

Figure 3:
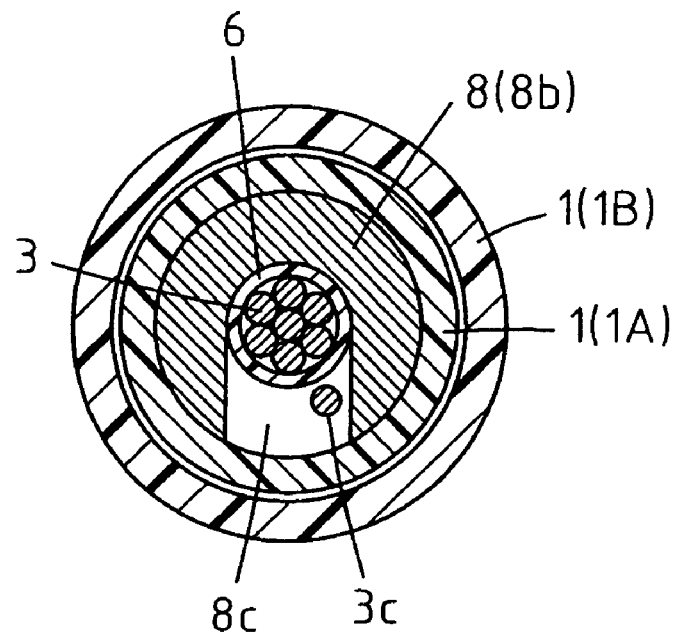
FIG. 3 is a cross sectional view taken along the III-III line shown in FIG. 1.

The endoscopic high-frequency knife is provided between the outer periphery of the conductive wire 3 and the inner periphery of the distal portion 1A (i.e., between the outer periphery of the sheath 6 and the inner periphery of the distal portion 1A) with a fixing member 8 for fixing the conductive wire 3 and the distal portion 1A to each other, as shown in FIG. 3 which shows a cross section taken along III-III line of in FIG. 1.

Figure 4:
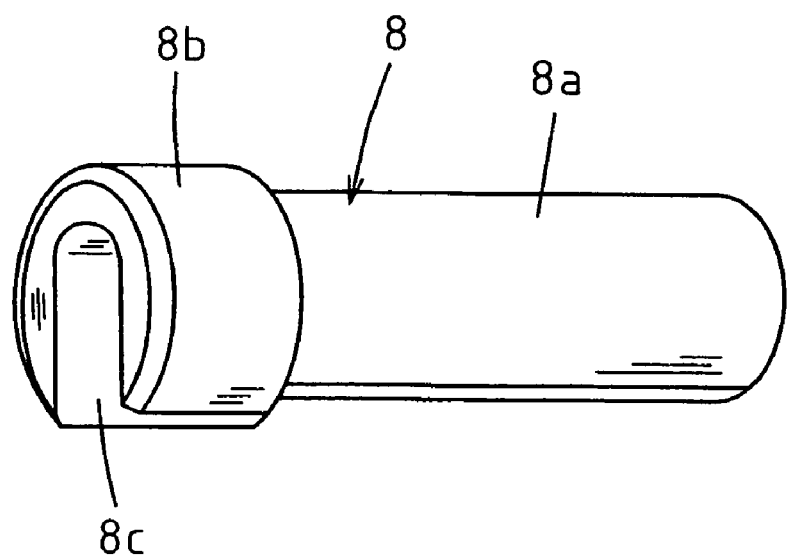
FIG. 4 is a perspective view of a fixing member of the endoscopic high-frequency knife shown in FIGS. 1 and 2.

As shown in FIG. 4, which shows the fixing member 8 in isolation from other elements of the endoscopic high-frequency knife, the fixing member 8 is provided with a hollow cylindrical portion 8a and an end portion 8b. The cylindrical portion 8a is formed to have substantially the same outer diameter as the inner diameter of the distal portion 1A, and the end portion 8b is formed at one end of the hollow cylindrical portion 8a to have an outer diameter slightly greater than the inner diameter of the distal portion 1A, so that the outer peripheral surface of the fixing member 8 is stepped between the hollow cylindrical portion 8a and the end portion 8b. The fixing member 8 can be made of metal or nonmetal.

Figure 5:
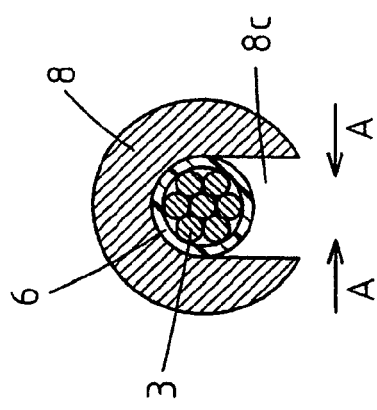
FIG. 5 is a cross sectional view of the endoscopic high-frequency knife shown in FIGS. 1 and 2, showing a state where a conductive wire is inserted into the fixing member shown in FIG. 4 and is fixed to the fixing member.

The fixing member 8 is provided with an axial groove 8c formed in a radial direction from an outer peripheral surface of the fixing member 8 to the axis thereof and elongated throughout the entire length of the fixing member 8 parallel to the axis thereof. As shown in FIG. 5, the conductive wire 3 sheathed with the sheath 6 is inserted into the axial groove 8c, and thereafter the fixing member 8 is swaged in directions to narrow the width of the axial groove 8c, as shown by arrows A in FIG. 5, to thereby fix the conductive wire 3 to the fixing member 8 in the axial groove 8c.

The fixing member 8 to which the conductive wire 3 is fixed in such a fixing manner is fixed to the distal portion 1A by press-fitting the large-diameter end portion 8b into the distal portion 1A from the rear end thereof, which causes a portion of the conductive wire 3 in the vicinity of the end thereof to be fixed to the distal portion 1A via the fixing member 8.

The extended part 3c of the conductive wire 3 which is positioned in the distal portion 1A behind the high-frequency cutting electrode 2 passes through the axial groove 8c of the fixing member 8 to protrude rearward from the fixing member 8.

A manual operation portion (not shown), with which one can manually rotate the conductive wire 3 about the axis thereof, is coupled to the proximal end of the proximal portion 1B. Electric current can be passed through the high-frequency cutting electrode 2 by connecting a line cord of a high-frequency power supply (not shown) to the manual operation portion.

In the present embodiment of the endoscopic high-frequency knife that is constructed in the above described manner, manually rotating the conductive wire 3 about the axis thereof in directions shown by double-headed arrows R in FIGS. 1 and 2 by the user causes the distal portion 1A to rotate about the axis thereof relative to the proximal portion 1B in directions shown by double-headed arrows r in FIGS. 1 and 2, thus causing the high-frequency cutting electrode 2 to rotate about the axis of the sheath 1.

Due to such a structure, in the case where one makes numerous consecutive incisions in, e.g., a swelled resection part of a mucosa with an endoscopic high-frequency knife, incisions can be easily made in the swelled resection part in a short time with the above illustrated embodiment of the endoscopic high-frequency knife. This is because one can reorient the high-frequency cutting electrode 2 to change the incisional position for the subsequent incising operation instantly by changing the orientation of the high-frequency cutting electrode 2 by approximately 180 degrees each time an incision has been made in the swelled resection part by swinging the flexible sheath 1 with the high-frequency cutting electrode 2 in an energized state.

Figure 6:
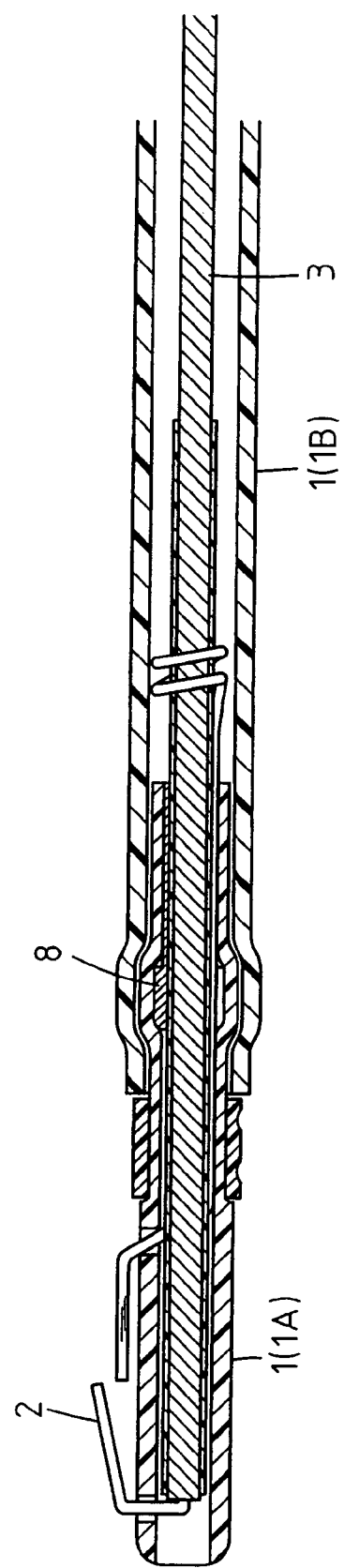
FIG. 6 is an axial sectional view of the end portion of the endoscopic high-frequency knife shown in FIGS. 1 and 2 in a state in which a high-frequency cutting electrode of the endoscopic high-frequency knife has broken.
Figure 7:
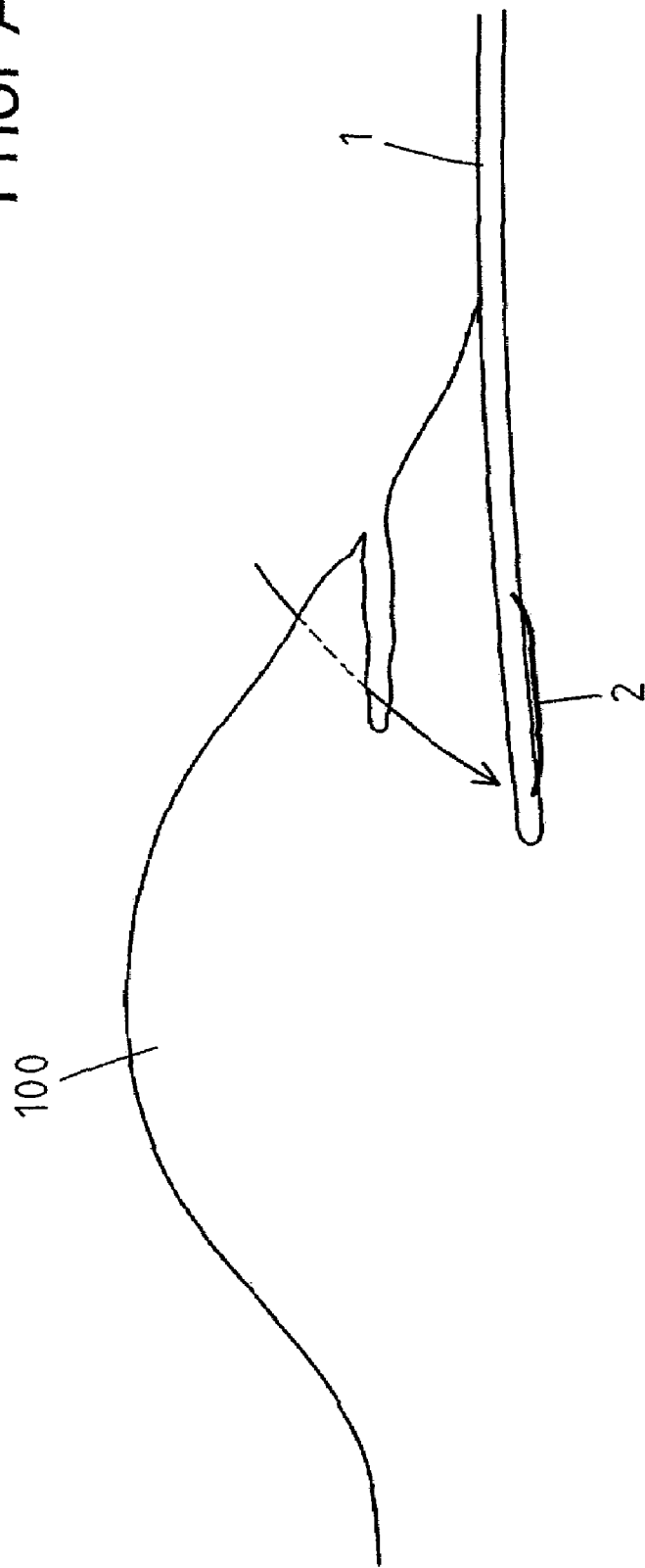
FIG. 7 is a diagram showing a state in which an endoscopic mucosal resection is performed with the use of a conventional endoscopic high-frequency knife.

Moreover, since the distal portion 1A is fixed relative to the conductive wire 3, there is no possibility of the distal portion 1A from falling off in the body of a patient even if the high-frequency cutting electrode 2 breaks during the resection operation in the patient body as shown in FIG. 6, which ensures a superior level of structural safety.

The present invention is not limited solely to the particular embodiment described above. Namely, the structure and the shape of the fixing member 8 are optional, i.e., the fixing member 8 only needs to serve as a fixing device which fixes the distal portion 1A and the conductive wire 3 to each other.

Obvious changes may be made in the specific embodiment of the present invention described herein, such modifications being within the spirit and scope of the invention claimed. It is indicated that all matter contained herein is illustrative and does not limit the scope of the present invention.

What is claimed is:

1. An endoscopic high-frequency knife, comprising:
   an insulating flexible sheath;
   a conductive wire inserted into said insulating flexible sheath; and
   a high-frequency cutting electrode,
   wherein said high-frequency cutting electrode is installed in said endoscopic high-frequency knife so that an outer surface of said high-frequency cutting electrode is exposed at a side surface of said insulating flexible sheath in the vicinity of an end thereof,
   wherein said conductive wire is electrically connected with said high-frequency cutting electrode,
   wherein said insulating flexible sheath includes a distal portion and a proximal portion which are separated from each other at a separation position behind said high-frequency cutting electrode on a proximal side thereof in the vicinity of said end of said insulating flexible sheath,
   wherein said distal portion and said proximal portion are connected to each other at said separation position to be freely rotatable relative to each other about a common axis which is also common with an axis of said insulating flexible sheath, so that said distal portion rotates about said common axis by rotating said conductive wire from a proximal end of said proximal portion,
   wherein a portion of said conductive wire in the vicinity of an end thereof is fixed to said distal portion to thereby prevent said distal portion from separating from said conductive wire even if said high-frequency cutting electrode breaks, and wherein an end of a core strand of said conductive wire, which is positioned in said proximal portion behind said high-frequency cutting electrode, is wound loosely around said conductive wire.

2. The endoscopic high-frequency knife according to claim 1, further comprising a fixing member which is fixed to said conductive wire in the vicinity of said end thereof, wherein said conductive wire is fixed to said distal portion by press-fitting said fixing member into said distal portion.

3. The endoscopic high-frequency knife according to claim 2, wherein an axial groove is formed in said fixing member from an outer peripheral surface of said fixing member to an axis thereof, said axial groove being elongated throughout the length of said fixing member and is parallel to said axis of said fixing member, wherein said conductive wire is inserted into said axial groove so as to be fixed to said fixing member.

4. The endoscopic high-frequency knife according to claim 3, wherein said conductive wire comprises a stranded wire including a plurality of wire strands, wherein at least one wire strand of said plurality of wire strands is extended and bent rearward in the vicinity of an end of said distal portion to be partly formed as said high-frequency cutting electrode, and wherein a rearward-extending part of the rearwardly bent said wire strand passes through said axial groove to extend rearward from said fixing portion.

5. The endoscopic high-frequency knife according to claim 4, wherein said wire strands are partly sheathed in the vicinity of an end thereof by a sheath which prevents said conductive wire from becoming frayed, wherein said fixing member is fitted directly on said sheath.

6. The endoscopic high-frequency knife according to claim 3, wherein said fixing member is swaged with said conductive wire, said conductive wire being positioned in said axial groove of said fixing member so as to fix said conductive wire to said fixing member.

7. The endoscopic high-frequency knife according to claim 2, wherein said fixing member has a substantially cylindrical shape and includes a small-diameter portion and a large-diameter portion provided at one end of said small-diameter portion, wherein an outer diameter of said small-diameter portion is substantially the same as an inner diameter of said distal portion of said insulating flexible sheath, and wherein an outer diameter of said large-diameter portion is slightly greater than said inner diameter of said distal portion, so that an outer peripheral surface of said fixing member is stepped between said small-diameter portion and said large-diameter portion.

8. The endoscopic high-frequency knife according to claim 1, wherein said core strand of said conductive wire is extended to be partly drawn out of said distal portion to serve as said high-frequency cutting electrode.

9. The endoscopic high-frequency knife according to claim 1, wherein said high-frequency cutting electrode extends in a direction substantially parallel to an axis of said distal portion.

10. The endoscopic high-frequency knife according to claim 9, wherein said distal portion includes two holes which are provided apart from each other in said direction substantially parallel to said axis of said distal portion, said outer surface of said high-frequency cutting electrode being exposed at said side surface of said insulating flexible sheath via said two holes.

* * * * *